United States Patent [19]

Fossetti

[11] Patent Number: 5,321,445

[45] Date of Patent: Jun. 14, 1994

[54] APPARATUS AND METHOD FOR VISUAL TRAINING AS A FUNCTION OF RETINAL REFLECTION

[76] Inventor: Alessandro Fossetti, Piazza Garibaldi No. 1,50053, Empoli, Italy

[21] Appl. No.: 980,745

[22] Filed: Nov. 24, 1992

[30] Foreign Application Priority Data

Nov. 26, 1991 [IT] Italy ............................ 279 A/91

[51] Int. Cl.$^5$ ............................................. A61B 3/00
[52] U.S. Cl. ................................. 351/203; 351/205; 128/630; 128/745
[58] Field of Search ............... 351/203, 205, 208, 210, 351/211, 212; 128/630, 745, 633

[56] References Cited

U.S. PATENT DOCUMENTS

| | | | |
|---|---|---|---|
| 4,305,398 | 12/1981 | Sawa | 128/633 |
| 4,533,221 | 8/1985 | Trachtman | 351/203 |
| 4,660,945 | 4/1987 | Trachtman | 351/203 |
| 5,002,384 | 3/1991 | Trachtman | 351/203 |

OTHER PUBLICATIONS

Learning of Visceral and Glandular Responses Science, vol. 163, pp. 434–445, Jan. 31, 1969, by Neal E. Miller.

Kruger, American Journal of Optometry and Physiological Optics, vol. 54, No. 10, Oct. 1977, Baltimore, USA pp. 673–677.

Rotberg, Survey of Ophthalmology, vol. 27, No. 6, May 1993 pp. 381–386.

Halperin & Yolton, American Journal of Optometry and Physiological Optics, vol. 63, No. 12, Dec. 1986, Baltimore, USA pp. 985–998.

Randle, Agard Conference Proceedings On Adaptation and Acclimatisation in Aerospace Medicine, No. 82, Sep. 1970.

E. B. Forrest, Stress and Vision, Optometric Extension Program Foundation, 1988.

R. A. Kraskin, Stress-Point Retinoscopy, J. Am. Optom. Ass. 1965; 36:69–72.

J. V. Basmajian, Biofeedback-Principles and practice for clinicians, 2nd ed. Baltimora: William & Wilkins, 1983.

R. J. Randle, Volitional control of on visual accommodation, Conference proceedings 82 aerospace medicine.

P. Kruger, Brightness Changes during Books Retinoscopy, Am. J. Optom. Physical, Opt. Oct. 1977; 54:673–677.

M. H. Rotberg, Biofeedback for ophthalmologic disorders, Surv. Opthalmol. 1983; 27:381–386.

E. Halprin & R. L. Yolton, Ophthalmic application of biofeedback, Am. J. Optom. Physical. Opt. 1986; 63:985–998.

J. N. Trachtman, V. Giambalvo, J. Feldman, Biofeedback of accommodation to reduce functional myopia, Biofeedback Selfregul. 1984; 4:547–64.

*Primary Examiner*—Loha Ben
*Attorney, Agent, or Firm*—McGlew and Tuttle

[57] ABSTRACT

A voluntary control, intended to obtain an increase in retinal reflection, is carried out using an auditory biofeedback technique based on the measurement of retinal reflection, for the purpose of achieving an improvement in visual perception in its principal functions; the method includes the following phases:

periodic measurement of the retinal reflection and of its variations, independently of factors concerning ocular optics;

production of a tone representative of such measurements, which informs the patient as to the condition and as to the variations of his own retinal reflection;

instruction on voluntarily increasing the retinal reflection by means of the voluntary control of the biofeedback tone.

11 Claims, 1 Drawing Sheet

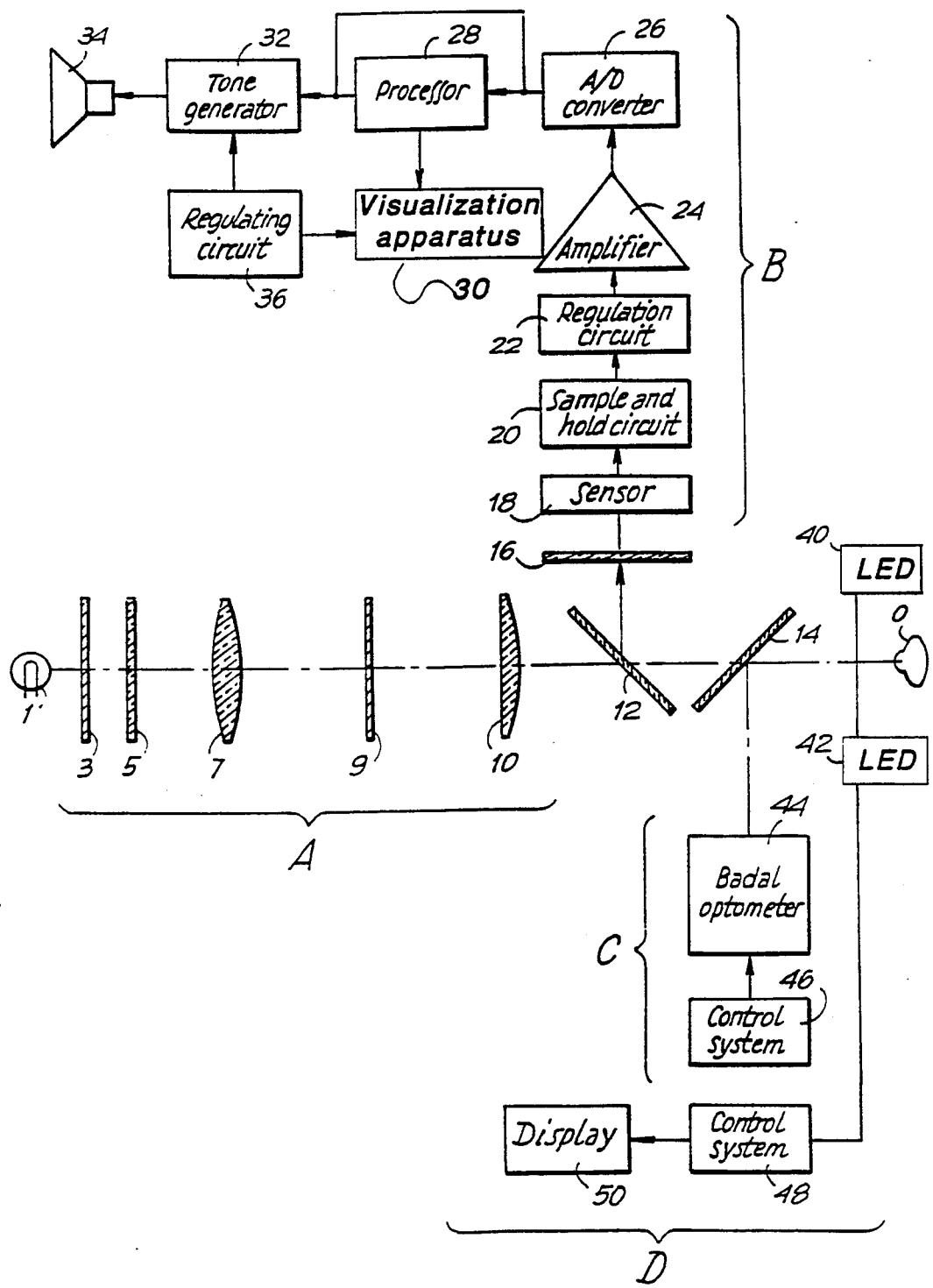

APPARATUS AND METHOD FOR VISUAL TRAINING AS A FUNCTION OF RETINAL REFLECTION

FIELD OF THE INVENTION

The invention relates to an apparatus and to a method for visual training, directed at the treatment and at the reduction of visual problems associated both with the mechanism of visual discrimination (and thus problems of clarity of vision, of visual acuity and of observation of the external world), and with the mechanism of ocular focusing (and thus problems of fatigue and of concentration), and also with the mechanism of ocular convergence (and thus with binocular balance and co-ordination).

BACKGROUND OF THE INVENTION

Visual training has been practiced for decades throughout the world by means of techniques of various types, and numerous instruments having differing operative characteristics are already available on the world market.

SUMMARY AND OBJECTS OF THE INVENTION

The apparatus and the technique forming the subject of the invention differ from the apparatuses and from the techniques utilized up to the present time in that they act on a function of the visual system which up to the present time has not been subjected to control in a visual training.

The function on which the action takes place is that of the capacity of the visual system—understood as the eye-brain unit—to modify the retinal reflection, independently of factors concerning ocular optics, in relation to the cognitive activity, to the perceptive attitude and, in particular, to visual concentration and attention. It is known that, when visual concentration and attention increase and the visual system is prepared to receive and to exploit to the greatest possible extent the information originating from the outside in the form of radiant energy, the reflection of such energy by the retina increases. The variations, in terms of energy, in the retinal reflection may readily be verified by means of simple objective techniques, such as retinoscopy. This phenomenon is well known in the optometric-ophthalmological sector and has been known for more than 30 years (D.B. Harmon: Notes on a dynamic theory of vision. 3rd ed. T.X. Austin,: Research Publication, 1958) and has been reported by various authors (R.A. Kraskin: Stress point retinoscopy, J.Am.Optom..Ass. 1965; 36:416–419./P. Kruger: Changes in fundus reflex luminance with increased cognitive processing. Am.J.Optom.Physiol.Opt. 1977;54:673–677./E.B. Forrest: Stress and vision, Santa Ana, Calif.: Optometric Extention Program Foundation, 1988).

When the retinal reflection increases, the visual system is under the best operative conditions and there is consequently an improved control concerning all the various functions which constitute visual perception, in particular concerning visual acuity, perception and control of the field of peripheral vision, stereopsis, focusing control, binocular control, attention, concentration and comprehension capacity. When there are visual problems of various types and, in particular, relating to the capacity for visual discrimination and for focusing, the retinal reflection is usually reduced and obscured and the subject does not succeed in tackling in the best way the visual tasks imposed by the sociocultural conditions in which he operates. To be able to increase the retinal reflection would mean, in these cases, being able to increase the capabilities for tackling these tasks and the visual problems which they involve, without having recourse to optical aids—such as spectacles, contact lenses or other aids—and especially without risking a continuous deterioration of the visual conditions.

Furthermore, the training aimed at increasing the capabilities of any visual function may become more effective if the subject places himself under such conditions as to have a brighter retinal reflection, i.e. under conditions such as to have the maximum performance levels in the various functions of the visual system.

The subject of the present invention is an apparatus and a method of biofeedback to provide instruction on voluntarily increasing the retinal reflection and to associate such an increase with visual training techniques aimed at the functions of focusing and of convergence.

The possibility of providing instruction on the voluntary control of functions of the body which are usually subject to the control of the neurovegetative system is known (N.E. Miller: Learning of visceral and glandular responses. Science 1969;163:434). To this end, use has for some time been made, for example, of techniques of galvanic, electromyographic and temperature biofeedback, for the voluntary control of specific muscular zones and of specific functions of the body (J.V. Basmajian: Biofeedback—Principles and practice for clinicians. 2nd ed. Baltimora: William & Wilkins, 1983).

With regard to the eye and the visual functions, biofeedback techniques have been utilized for the control of the extrinsic musculature and for the voluntary control of accommodation (R.J. Randle: Volitional control of visual accommodation. Conference proceedings 82 on aerospace medicine. AGARD, NATO, Garmisch-Partenkirchen, Sep. 14–18, 1970. // J.N. Trachtman, V. Giambalvo, J. Feldman: Biofeedback of accommodation to reduce functional myopia. Biofeedback Selfregul. 1984;4:547–64. // M.H. Rothberg Biofeedback for ophthalmologic disorders. Surv.Ophthalmol. 1983;27: 381–6. // E. Haperin, R.L. Yolton: Ophthalmic application of biofeedback. Am.J.Optom.Physiol.Opt 1986;63:985–98).

Thus, the present invention is fundamentally based on the criterion of influencing the subject to carry out voluntary control of the retinal reflection, and specifically to provide instruction on increasing the same by making use of an auditory biofeedback technique based on the measurement of retinal reflection.

In practice, a narrow beam of infrared radiation is passed to the retina of the subject. The reflection of such radiation by the retina is passed to a suitable sensor, which measures the energy level thereof. This level is then communicated to the patient in the form of a sound signal which varies, for example, in volume and/or in frequency, in accordance with the energy level measured and thus the intensity of the retinal reflection varies. When the retinal reflection increases, the volume or the frequency of the sound signal also increases and vice versa. The patient is thus continuously informed as to the conditions of his retinal reflection, and can learn to control the same by means of the control, i.e. the response offered by the sound signal.

The beam of infrared radiations which is projected onto the retina may have, in transverse section, linear dimensions of the order of 0.7 mm at the pupillary plane. In this way, as is well known in the optometric ophthalmological field, there is complete elimination of the influence of the accommodative mechanism on the focusing of the beam of radiations and thus on the variation of retinal reflection. There is furthermore elimination of the influence of the variations in the pupil diameter on the beam of radiations.

The training is carried out on a monocular basis and is initiated in the dark without the presentation of any target to the subject. In this way, the subject is taught to control the retinal reflection independently of any other visual function, and, in particular, independently of any influence due to accommodation.

In the subsequent phases, once the subject has learned to increase his own retinal reflection, there is associated with the reflection of the beam of infrared radiation the presentation of targets suitable for stimulating both the mechanism of focusing and that of convergence. In this way, these visual functions may be trained under the best operative and control conditions, i.e. with the maximum possible retinal reflection, permitting the achievement of more rapid and greater results than those which are possible using the visual training techniques utilized up to the present time.

The training of the focusing function may in practice be carried out with the use of a Badal optometer, by means of which it is possible to present to the subject targets which are placed at differing optical distances and which thus require differing amounts of accommodation, as is well known in the optometric ophthalmological field.

The training of the convergence may advantageously be carried out by means of the presentation of luminous targets to the eye which is contralateral to that subjected to retinal-reflection biofeedback. The targets may be presented at differing distances from the contralateral eye, depending upon the distance between the visual axes of the subject and upon the requirements of the case. The subject is then requested to superpose the images of the two eyes, thus modifying his own convergence; this is known in the optometric-ophthalmological field.

In order to obtain results which are evident from the present text, the subject of the invention is substantially a method of visual training to increase the capabilities of the visual functions, which method comprises the activation of the retinal reflection by means of biofeedback to train for the increasing of such reflection and to associate such increase with visual training techniques which are aimed specifically at the functions of focusing and of convergence.

In practice, the method provides a voluntary control intended to obtain an increase in the retinal reflection, carried out using an auditory biofeedback technique based on the measurement of the retinal reflection.

The method of visual training concerned—which is directed at improving the visual perception in its principal functions—is in practice composed of the following phases:

periodic measurement of the retinal reflection and of its variations, independently of factors concerning ocular optics;

production of a tone representative of such measurements, which informs the patient as to the condition and as to the variations of his own retinal reflection;

instruction on voluntarily increasing the retinal reflection by means of voluntary control of the biofeedback tone.

The method may comprise the further phases of:

presentation of targets suitable for stimulating the focusing mechanism of focusing and thus for training with regard to a multiplicity of problems and of disorders linked to ocular accommodation;

presentation of targets suitable for stimulating the ocular convergence mechanism and thus for training with regard to a multiplicity of disorders linked to binocular muscular coordination.

In a practical embodiment, a narrow beam of infrared radiations is passed on a monocular basis to the retina without influencing the accommodative mechanism; the beam reflected by the retina is subjected to a processing to obtain signals able to generate a tone, the characteristics of which are linked to the magnitude of the signals and/or a corresponding visual-perceptive condition; the tone and/or the visual-perceptive condition may be corrected by the patient.

A narrow beam of infrared radiation may be passed to the retina of the subject. The reflection of such radiation effected by the retina is passed to a suitable sensor, which measures the energy level thereof. The level is communicated to the patient in the form of a sound signal which varies—in volume and/or in frequency—as the energy level measured and thus the intensity of the retinal reflection varies, in the sense that as the retinal reflection increases the volume or the frequency of the sound signal also increases and/or vice versa, to inform the patient continuously as to the conditions of his retinal reflection, as a result of which he is led to control the same by means of the control of the sound signal.

A further subject of the invention is an apparatus for visual training, which substantially comprises: a device for measuring the reflection or reflectivity of the central retina and its variations, independently of factors concerning ocular optics, an apparatus for producing biofeedback tones, which provides information, directly and in real time, on the condition of and on the variations in the retinal reflection, with a generator of frequencies which are proportional to and/or representative of the readings made by the sensor of the device for measuring the retinal reflection; an apparatus for the graphical-numerical visualization of the readings made by the device, with data which are representative of the condition and of the variations in the retinal reflection, independently of factors concerning ocular optics.

The device for measuring the reflection of the retina may, in practice, comprise: a radiation source; an optical system capable of projecting onto the retina a beam of radiations with a circular cross section having dimensions equal to or less than a diameter of 0.7 mm in the pupillary plane, in such a manner that the path of such radiations is not influenced either by ocular accommodation or by the variations in the pupil diameter; and a sensor capable of periodically reading the intensity of the radiant energy reflected by the retina and of converting such readings into electrical signals corresponding and proportional to the distribution of the radiant energy passed to the sensor.

The apparatus may further comprise an apparatus for the presentation of targets for the stimulation of the focusing mechanism and for the training of the ocular accommodation in conjunction with the biofeedback of the retinal reflection, as well as an apparatus for the presentation of luminous targets for the control, the stimulation and the training of the convergence in conjunction with the biofeedback of the retinal reflection.

The invention will be better understood according to the description and the accompanying drawing, which shows a practical nonlimiting illustrative embodiment of the invention. The drawing shows the diagram of the apparatus with optical and electronic symbology.

DETAILED DESCRIPTION OF THE PREFERRED EMBODIMENT

The apparatus as shown in the drawing exhibits: an optical system or means A for producing the beam of infrared radiation required for the measurement of the retinal reflection; an electronic system or processing means B for the management, the control and the visualization of the measurements made, as well as for the generation of the tone which is necessary for the biofeedback procedure; an apparatus C for the presentation, to the subject, of targets suitable for training the focusing system; and an apparatus D for the presentation, to the subject, of targets suitable for training the convergence system, with right-hand and left-hand luminous targets, which are defined in greater detail hereinbelow.

Briefly, the optical system A is made up of: a source 1, such as a conventional tungsten lamp, emitting in the visible and in the infrared; a circular diaphragm 3; an infrared filter 5; an achromatic converging lens 7; a further circular diaphragm 9; an achromatic converging doublet 10. This assembly generates a beam of parallel infrared radiations, of mainly circular cross section, of linear dimensions of the order of 0.7 mm. A semireflecting mirror 12 and a semireflecting mirror 14 are positional between the optical system and the eye O. The semi-reflecting mirror 14 having a maximum transmission of infrared wavelengths. Both semi-reflecting mirrors being arranged at an inclination of substantially 45° with respect to the beam of infrared radiation and an axis of the optical system. The mirror 12 partially deflects the return beam toward an achromatic converging doublet 16 and onto an infrared sensor 18 of the system B. The mirror 14 only very partially deflects the return beam toward the apparatus C.

More particularly, the radiant energy emitted by the lamp 1 and diaphragm-controlled by the circular aperture of the diaphragm 3 is filtered by the filter 5, which transmits radiations outside the visible range, with a maximum at 930 nm. Thus, the infrared radiation reaches the lens 7 in the form of a divergent beam. The lenses 7 and 10 act on the beam of radiations in such a manner as to make them parallel; these thus constitute an achromatic a focal system. The beam of parallel radiations passes through the semireflecting mirrors 12 and 14 and is passed to the eye O. The circular diaphragm 9, which is placed in the path of the beam of radiations, has the effect of diaphragm-controlling the beam of radiation and of providing, in the pupillary plane of the eye O, a circular image having linear dimensions of 0.7 mm. In this way (as is known in the optical and ophthalmological field) it is as if a stenopeic aperture were placed in front of the eye. This condition assures the elimination of the influence of factors concerning ocular optics on the beam of infrared radiation and, in particular, both of the accommodation and of the variations in the pupil diameter.

The infrared radiation penetrating into the eye O is reflected by the retina and, after having passed through the semireflecting mirror 14, is passed from the semireflecting mirror 12 toward the achromatic doublet 16, which focuses it onto the sensor 18. The sensor 18 is sensitive to infrared wavelengths, and emits a voltage which is variable in relation to the intensity of the incident radiation, which is an analog signal which is processed and exploited by the system B.

In a practical embodiment, the lenses 7 and 10 have a focal length of 50 mm; the lens 7 is placed at 100 nm from the lamp 1, and the lens 10 is placed at 150 mm from the lens 7, in such a manner as to produce a beam of parallel radiations. The diaphragm 9 is situated at a distance of 75 mm from the lens 10, in such a manner as to produce a circular image of 0.7 mm at 150 mm from the lens 10 and at this distance is positioned the pupillary plane of the eye O. The lens 10, which is composed of an achromatic doublet, has a focal length of 40 mm, and the sensor 18 is placed at a distance from the lens 16 which is greater than its focal length, for example 60 mm. The arrangement is nevertheless such as to permit projection, onto the sensor 18, of a sufficiently extensive image of the circular image reflected by the retina, so that the incident energy is able to activate an area of the sensor 18 such as to be able to produce signals which may readily be managed by the electronic system B, of which the sensor 18 represents the input.

The sensor 18 receives the infrared radiation reflected by the retina, and executes a certain number of readings per second, generating for each reading, a voltage signal the value of which is proportional to the radiant energy incident on the sensor. In practice, it is possible to use a conventional sensor incorporating silicon photodiodes, which is sensitive to infrared radiation and is regulated in such a manner as to execute the readings of the incident energy for example every 17 milliseconds, i.e. 58 times a second.

The voltage signals emitted by the sensor 18, which are proportional to the intensity of the radiation reflected by the retina, are passed to a circuit referred to as a sample-and-hold circuit 20, in this particular case an integrated circuit which is conventionally utilized for these purposes. The signals at the output of the sample-and-hold circuit 20 are first passed to a zero regulation circuit 22 and then amplified, by means of an amplifier 24. The amplified signals are passed to an A/D converter 26; this apparatus permits the conversion of the analog signals into digital signals, so that the values at the output of the amplifier 24 in the form of a variable voltage are converted into digital signals which can be utilized by a computer. Once converted into digital form, the signals are passed to a data processor 28. The processor 28 receives the data passed from the converter 26, processes them and passes them both to a visualization apparatus 30 with a monitor and display, and to a tone generator 32 with an associated emitter 34. The visualization of the data relating to the intensity and variation of the signal at the output of the sensor, and thus to the intensity and variation of the retinal reflection, may in fact be effected either in graphical form or in numerical form. It may be chosen to adopt both solutions, utilizing a common monitor for the graphical visualization and a display for the numerical visualization. The monitor visualizes a graph which reproduces the distribution of the radiant energy incident on the sensor 18 and its variations. The display visualizes numerical values which are proportional to the intensity of the radiant energy incident on the sensor 18. Thus, both the monitor and the display give information on the quality, quantity and variation of the energy passed from the retina to the sensor 18 and consequently on the quality, quantity and variation of the retinal reflection. The tone generator 32 utilizes the signals passed from the processor 26 for the purpose of generating frequencies which are proportional to the energy levels read by the sensor 18. These signals are then emitted by means of the loudspeaker 34.

Both the tone generator 32 and the system for visualizing the data 30 are controlled by a regulating circuit 36 which permits the variation of the characteristics both of the tones emitted by the loudspeaker 34 and of the graphs or of the numerical values visualized at 30.

The apparatus C is suitable for the presentation of targets placed at differing optical distances from the eye O and for which differing amounts of accommodation are required. This apparatus may be a simple and well known Badal optometer 44, having its optical axis coincident with the optical axis of the optical measurement system in the branch reflected by the semireflecting mirror 14. The Badal optometer 44 is provided with a control system 46 which permits the management of the presentation of the targets, both with regard to the optical distance and with regard to their size.

The apparatus D is suitable for presenting targets for the control and the training of the convergence function. The targets are formed by the two series of red LEDs 40 and 42, each having dimensions of 1/10 inch, the emission of which is made diffuse. The two series of luminous targets are situated one to the right and one to the left of the optical axis of the central system A, and may be presented both to the right eye and to the left eye, depending upon the particular case. The two series of targets 40 and 42 may be connected to a control system 48, which permits the variation of the distance of the activated target from the optical axis of the central system A, the variation of the luminance of the target in relation to the operative requirements, the alternation of the lighting up of the targets for the right or for the left eye, and the commanding of the visualization of the data relating to the position of the activated target on the appropriate visualization display 50.

It is understood that the drawing shows only an illustrative embodiment given solely by way of practical demonstration of the invention, it being possible for this invention to vary in terms of forms and arrangements without thereby departing from the scope of the concept which forms the basis of the invention.

I claim:

1. A method of visual training for increasing visual abilities of a patient, the method comprising the steps of:
   measuring an intensity of retinal reflectability of an eye of the patient;
   generating an auditory signal proportional to said intensity of retinal reflectability;
   using said auditory signal as a biofeedback technique to voluntarily control and increase said intensity of retinal reflectability of the patient and thus increase the visual abilities of the patient.

2. A method in accordance with claim 1, further comprising the steps of:
   passing a beam of infrared radiation onto the retina without activating an accommodation mechanism of the patient;
   receiving a reflected beam of infrared radiation reflected from the retina, said step of measuring said intensity of retinal reflectability being performed by measuring an intensity of said reflected beam of infrared radiation.

3. The method as claimed in claim 2, wherein:
   said beam of infrared radiation which is projected onto the retina has, in a transverse section, dimensions equal to or less than 0.7 mm in a pupillary plane of the patient, said dimensions substantially eliminate an influence of the accommodation mechanism of the patient focusing said beam of infrared radiation and thus stopping said accommodation mechanism from varying said retinal reflectability, there being furthermore a substantial elimination of an influence of variations in pupil diameter on said infrared beam of radiation.

4. A method in accordance with claim 2, further comprising the steps of:
   providing a sensor means for measuring an energy level of said reflected beam of infrared radiation, said energy level being proportional to said retinal reflectability;
   said auditory signal being proportional to said energy level and retinal reflectability, said auditory signal varying in one of volume and frequency in proportion to said energy level.

5. A method in accordance with claim 1, wherein:
   said steps of measuring intensity of retinal reflectability, generating an auditory signal, and using said auditory signal as a biofeedback technique, are initially performed in a dark condition without targets being presented to the patient;
   subsequent to said steps in said dark condition, presenting targets to said patient for stimulating focusing and convergence mechanisms of the patient.

6. A method of visual training for increasing visual abilities of a patient, the method comprising the steps of:
   periodically measuring an intensity of retinal reflectability of an eye of the patient substantially independent of effects caused by ocular optics;
   generating an auditory tonal signal proportional to said intensity of retinal reflectability;
   instructing the patient to voluntarily increase said retinal reflectability by listening to said auditory tonal signal and voluntarily controlling said auditory tonal signal to indicate increased retinal reflectability thus increase the visual abilities of the patient.

7. The visual training method as claimed in claim 6, which comprises the further steps of:
   presenting targets suitable for stimulating a focusing mechanism of the patient;
   training the focusing mechanism of the patient with regard to a multiplicity of problems and disorders linked to ocular accommodation;
   presenting targets suitable for stimulating an ocular convergence mechanism of the patient;
   training the ocular convergence mechanism with regard to a multiplicity of disorders linked to binocular muscular coordination.

8. An apparatus for visual training to increase visual abilities of a patient, the apparatus comprising:
   optical means for projecting a beam of radiation onto a retina of an eye of the patient, said beam having a diameter of less than or equal to 0.7 mm in a pupillary plane of the eye, said beam being substantially unaffected by ocular accommodation and variations in pupil diameter of the eye;
   sensor means for receiving a reflected beam of radiation reflected from the retina and for measuring an intensity of said reflected beam of radiation proportional to a reflectability of the retina and substantially independent of ocular optic effects;

processing means for reading said sensor means and generating an auditory signal proportional to said intensity of said reflected beam of radiation and the reflectability of the retina;

visualization means for graphical visualization of said intensity of said reflected beam of radiation and the reflectability of the retina substantially independent of ocular optic effects.

9. The apparatus at least as claimed in claim 8, further comprising:

focusing target means for presenting targets to stimulate a focusing mechanism of the eye and for training of ocular accommodation in conjunction with said auditory signal.

10. The apparatus at least as claimed in claim 8, further comprising:

convergence target means for presenting luminous targets to control stimulation and training of convergence in conjunction with said auditory signal.

11. A device in accordance with claim 8, wherein:

said processor means varies a frequency of said auditory signal in proportion to said intensity of said reflected beam.

* * * * *